United States Patent [19]
Rothenberg et al.

[11] Patent Number: 6,145,667
[45] Date of Patent: Nov. 14, 2000

[54] MINERAL COLLECTOR COMPOSITIONS AND PROCESSES FOR MAKING AND USING SAME

[75] Inventors: Alan S. Rothenberg, Wilton; Lino Giovanni Magliocco, Shelton, both of Conn.

[73] Assignee: Cytec Technology Corp., Stamford, Conn.

[21] Appl. No.: 09/085,364

[22] Filed: May 27, 1998

[51] Int. Cl.$^7$ .............................. B03D 1/01; B03D 1/006; B03D 1/02
[52] U.S. Cl. ................................. 209/166; 252/61
[58] Field of Search ..................... 252/61; 209/166, 209/167

[56] References Cited

U.S. PATENT DOCUMENTS

| | | |
|---|---|---|
| 3,464,784 | 9/1969 | Swanson . |
| 3,933,872 | 1/1976 | Hartlage . |
| 4,629,556 | 12/1986 | Yoon et al. . |
| 4,834,951 | 5/1989 | Schwab et al. . |
| 4,871,466 | 10/1989 | Wang et al. . |
| 5,126,038 | 6/1992 | Nagaraj . |
| 5,237,079 | 8/1993 | Wang et al. . |
| 5,260,039 | 11/1993 | Schwab et al. . |
| 5,522,986 | 6/1996 | Shi et al. . |
| 5,632,963 | 5/1997 | Schwab et al. . |

FOREIGN PATENT DOCUMENTS

| | | |
|---|---|---|
| 982810 | 12/1982 | U.S.S.R. . |

OTHER PUBLICATIONS

Dekun, Jingquig and Weizhi, Application of hydroxamic acid and hydroxamic—xanthate, collector system in metal ore flotation, *Reagents in the Minerals Industry*, edited by Jones and Oblatt, pp. 169–172, 1984.

XP–002109781 Derwent: SU–956022, Carbonate Silicide Phosphorite Ore Concentrate Alkyl Sulphonate Surfactant Specified Ratio Modified, Jul. 9, 1982.

XP–002109782/Derwent: SU–5139070, Alkyl Hydroxamic Acid Flotation Agent Produce Correspond Carboxylic Acid Alkali Separate Mineral Acid Hydrocarbon, Jul. 2, 1996.

XP–002109780 Derwent: Zho Weizhi, On the Flotation of Lean iron Ore with Hydroxamic Acid, Oct. 19,1985, pp. 248–249.

Fuerstenau and Pradip, Mineral Flotation with Hydroxamate Collectors, *Reagents in the Minerals Industry*, Ed. M.J. Jones and R. Oblatt, Inst. Min. Met., London, 1984, pp. 161–168.

*Organic Synthesis,* vol. 11, p. 67.

Gorlovski, et al., Vses. Soveshch. po Sintetich. Zhirozamenitelyam, Poverkhnostnoaktivn, Veschestvam i Moyushchim Sredstvam, 3rd, Sb., Shebekino, 1965, 297–9 Chem. Abst. 66, 4983g, 1967.

Shchukina et al., in Sin. Primen. Novykh Proverkh. Veshchestv, 1973, 123–31, C.A. 80, 1974, 95199K.

Russian Patent No. 390,074, Chem. Abst. 79, 115162C (1973).

Russian Patent No. 513,970, May 15, 1976, Chem. Abst. 85, 66277g, 1976.

*Primary Examiner*—Thomas M. Lithgow

[57] ABSTRACT

Collector compositions of a mixture of a $C_6$ to $C_{22}$ fatty hydroxamic acid and an oil for use in the removal of impurities from mineral ores by the froth flotation method. The collectors are prepared by reacting an ester of a $C_6$ to $C_{22}$ fatty acid with a hydroxylamine salt and a base in the presence of an oil and water to produce an alkyl hydroxamate salt; acidifying the alkyl hydroxamate salt, forming an organic layer and an aqueous layer, wherein the organic layer contains a $C_6$ to $C_{22}$ fatty hydroxamic acid substantially free of starting esters and hydrolysis and transesterification products of the ester; and separating the organic layer from the aqueous layer to provide a collector composition of the $C_6$ to $C_{22}$ fatty hydroxamic acid and the oil.

11 Claims, No Drawings

MINERAL COLLECTOR COMPOSITIONS AND PROCESSES FOR MAKING AND USING SAME

BACKGROUND OF THE INVENTION

Alkyl or alkaryl hydroxamic acids and their salts are well-known collectors for the froth flotation of oxide minerals. Soviet workers have found a variety of applications for such alkyl hydroxamic acids, such as those described by Pradip and Fuerstenau, Mineral Flotation with Hydroxamate Collectors, *Reagents in the Minerals Industry*, Ed. M. J. Jones and R. Oblatt, Inst. Min. Met., London, 1984, pp. 161–168, a recent review that summarizes the flotation application of alkyl hydroxamic acids.

Hydroxamic acids have been used for the flotation of metals or minerals such as pyrochlore, fluorite, huebnerite, wolframite, cassiterite, muscovite, phosphorite, hematite, pyrolusite, rhodonite, chrysocolla, malachite, barite, calcite, and rare-earths. They are generally more powerful and more selective then conventional fatty acids, fatty amines, petroleum sulfonates and alkyl sulfates. However, the commercially employed methods of making alkyl or alkaryl hydroxamic acid or its salts are tedious and unsafe from the point of view of industrial production.

A procedure for making potassium alkyl hydroxamate is disclosed in *Organic Synthesis*, Vol. II, page 67. In the disclosed process, solutions of KOH and $NH_2OH$—HCl in methanol are combined. After the KCl byproduct is filtered off, the filtrate is combined with a liquid mixture of methyl caprylate and methyl caprate, and, after standing for 24 hours, the product crystals are filtered off. Major drawbacks of this method include low yields, the use of a large amount of toxic and flammable methanol, and the use of potassium hydroxide, which is more expensive than sodium hydroxide. In addition, the industrial scale filtration of a methanolic reaction mixture is clearly undesirable from a safety standpoint.

U.S. Pat. No. 3,933,872 to Hartlage claims an improved method of making fatty hydroxamates. Hydroxylamine sulfate and the methyl ester of a fatty acid are reacted in the presence of dimethylamine in an anhydrous lower alcohol slurry. The free hydroxamic acids formed are neutralized with dimethylamine or an alkali metal base to yield an ammonium or alkali metal salt, which precipitates, and is filtered and dried. However, the disclosed procedure also employs flammable lower alcohols, such as methanol, ethanol or isopropanol, requiring the filtration of the final hydroxamic product, which is hazardous. Moreover, because of the heterogeneous nature of the reaction, the reaction rate is very slow, e.g., on the order 15 hours in methanol and 5 days in isopropyl alcohol, and the yields are relatively low, i.e., on the order of about 75 percent.

Various Russian workers have reported methods for making alkyl hydroxamic acids and their salts in aqueous alkaline media. Gorlovski, et al., Vses. Soveshch. po Sintetich. Zhirozamenitelyam, Poverkhnostnoaktivn, Veschestvam i Moyushchim Sredstvam, 3rd, Sb., Shebekino, 1965, 297–9 Chem. Abst. 66, 4983h, 1967, report the production of sodium alkyl hydroxamates by reacting the methyl ester of a $C_{7,9}$ carboxylic acid with an aqueous solution of hydroxylamine sulfate and NaOH at a molar ratio of 1:1.22:2.2 and a temperature of 55° C. or below.

Shchukina et. al., Khim. Prom., Moscow, 1970, 49(3) 220, report a yield of only 72 to 78 percent of the free $C_{7,9}$ hydroxamic acid by reacting the methyl ester, hydroxylamine sulfate, and sodium hydroxide for two hours at 20°–25° C. and one hour at 55°–60° C., followed by acidification to pH 4–5 at temperatures below 40° C. Shchukina et al., in Sin. Primen. Novykh Proverkh. Veshchestv, 1973, 123–31 reported in C.A. 80, 1974, 95199K, also report a simple lab method for the production of a reagent designated as IM-50 from $C_{7,9}$ esters.

Russian workers, in Russian Patent No. 390,074, Chem. Abst. 79, 115162C (1973), and in Zh. Prikl, Khim, (Leningrad) 1972 45(8), 1895–7, Chem. Abstract 78, 29193m 1973, report improved yields with the use of 3 to 5 percent of an anionic emulsifier in an alkaline aqueous medium. The use of an anionic surfactant such as sodium lauryl sulfate (3–5 percent based on the weight of the methyl ester), reportedly gave an improved yield of 61.2 percent for valerihydroaxmic acid and 89 percent for caprihydroxamic acid. To obtain the claimed yields, however, a 40 molar percent excess of hydroxylamine hydrochloride or sulfate was required. Moreover, both the sodium salts and the free hydroxamic acids recovered are solids, which are difficult to handle and process.

Russian Patent No. 513,970, May 15, 1976, Chem. Abst. 85, 66277g, 1976, discloses the formation of a solution of mixed free $C_3$ to $C_{11}$ hydroxamic acids in hydrocarbons for use as a flotation agent. The disclosed hydroxamic acids were formed by treating carboxylate esters with the sulfate salt of hydroxylamine in an alkali medium, and then treating the resulting sodium alkyl hydroxamates with a mineral acid in the presence of 100–250 weight percent of a hydrocarbon containing less than 20 percent polar organic components, e.g., higher alcohols or esters. The aqueous layer containing NaCl or $Na_2SO_4$ was discarded as effluent. Because of the incomplete reaction of the starting ester, this process is inefficient, producing a product that contains significant quantities of the unreacted starting ester.

U.S. Pat. No. 4,629,556 discloses the removal of various colored impurities from kaolin clays utilizing alkyl, aryl or alkyl aryl hydroxamates as collectors. The disclosed hydroxamates are produced by reacting free hydroxylamine with the methyl ester of an organic acid having an appropriate length hydrocarbon chain and configuration in a non-aqueous medium, such as methanol, in a manner similar to the methods discussed above.

U.S. Pat. No. 4,871,466 discloses a method for the production of alkyl or alkaryl hydroxamic acids and/or salts. In the disclosed method, the methyl or ethyl ester of a fatty acid having 6 to 22 carbon atoms is reacted with a hydroxylamine salt and an alkali metal hydroxide in the presence of a mixture of water, a $C_8$ to $C_{22}$ alcohol, and, preferably, a non-ionic or cationic surfactant. The disclosed reaction results in the formation of a hydroxamate solution, which can be used without further processing in the froth flotation of non-sulfide minerals, or acidified to form a liquid alcohol solution of the acid before use in the flotation process. The disclosed process eliminates the need for hazardous and expensive recovery steps, such as filtration, it is relatively rapid, taking only three to five hours for completion, and provides relatively high conversions to hydroxamates. However, the final product of the disclosed method contains some unreacted starting ester.

Improvements in the industrial production and performance of the alkyl hydroxamate collectors are still required. For example, the handling of solid products is difficult in large scale of production, and increases the complexity and cost of manufacturing. Although this problem may be overcome by carrying out the reaction in the presence of alcohols, as taught in U.S. Pat. No. 4,871,466, as discussed above, the use of $C_8$ to $C_{22}$ alcohols leads to reduced yields through the competing reaction of transesterification and hydrolysis of the methyl esters, e.g., carboxylic acids and other carbonyl components derived from the starting ester. In addition, where hydroxamic acid collectors are used in the flotation process, the shorter chain alcohols, e.g., $C_8$, can produce uncontrollable frothing or produce undesirable froth properties, enhancing the recovery of undesirable minerals, and longer chain alcohols, i.e., $C_{10}$ and above, can reduce frothing substantially, which is a serious concern in column flotation where a certain amount of controlled froth phase is necessary. Furthermore, in certain applications, depending on the value mineral being floated, the higher alcohols can adsorb on the value mineral in a reverse configuration, i.e. they can adsorb with the polar group exposed to the water phase, thereby reducing hydrophobicity on the value mineral being imparted by the alkyl hydroxamic acid, resulting in the reduced recovery of the value mineral. The commercial alcohols, which can be expensive, also have a very strong, sometimes offensive odor, which varies with chain length.

Therefore, there remains a need for alkyl hydroxamic acid collectors and a process for preparing such collectors that overcome the problems discussed above. The present invention provides such collectors and a process for preparing them.

SUMMARY OF THE INVENTION

The invention is directed to collector compositions for use in the removal of impurities from mineral ores, and to methods for making and using such collector compositions. Typically, a collector composition of the invention comprises a mixture of a $C_6$ to $C_{22}$ fatty hydroxamic acid and an oil, where the oil is preferably selected from the group consisting of hydrocarbon, vegetable, plant, and animal oils, and is most preferably a fatty triglyceride oil. Preferred hydrocarbon oils include, but are not limited to aliphatic hydrocarbons, aromatic hydrocarbons, and mixtures thereof, such as benzene, xylene, toluene, mineral oil fractions, kerosene, naphthas, and petroleum fractions.

Preferably, the hydroxamic acid is present in the compositions of the invention in an amount of from about 5 to about 70 percent by weight, more preferably from about 10 to about 50 percent by weight, and the oil is present in an amount of from about 10 to about 95 percent by weight, more preferably from about 20 to about 70 percent by weight, based upon the weight of the composition. Optionally, the collector composition further comprises up to about 70 percent, preferably, from about 10 to about 50 percent by weight, of a frother.

The collector compositions of the invention may be prepared by reacting an ester of a $C_6$ to $C_{22}$ fatty acid with a hydroxylamine salt, preferably, a sulfate or hydrochloride salt of hydroxylamine, and a base in the presence of an oil and water to produce an alkyl hydroxamate salt. The alkyl hydroxamate salt is then acidified, forming an organic layer and an aqueous layer, where the organic layer contains a $C_6$ to $C_{22}$ fatty hydroxamic acid substantially free of hydrolysis and transesterification products of the ester, and the organic layer is separated from the aqueous layer to provide a mineral collector composition, comprising a mixture of the $C_6$ to $C_{22}$ fatty hydroxamic acid and the oil.

The benefication performance of the collector compositions of the invention is significantly improved when compared to prior art compositions, due to a lack of alcohol and a substantially reduced amount of fatty or starting ester in the collector compositions. Generally, the collector compositions of the invention are substantially free of starting ester, such that the amount by weight of $C_6$ to $C_{22}$ fatty acid ester or starting ester is less than the amount by weight of hydroxamic acid. Typically the amount of fatty acid ester or starting ester present in the collector compositions of the invention is 50 percent less than the amount of hydroxamic acid, preferably, less than 20 percent, and, most preferably, less than 10 percent of the amount of hydroxamic acid.

Esters useful in the process of forming the collector compositions of the invention include, but are not limited to, methyl and ethyl esters of caproic acids, enanthic acid, caprylic acid, pelargonic acid, caproic acid, undecanoic acid, lauric acid, tridecanoic acid, myristic acid, pentadeconic acid, palmitic acid, margaric acid, stearic acid, oleic acid, benzoic acid, ethyl benzoic acid, salicylic acid, α-naphthoic acid, β-naphthoic acid, cyclohexyl carboxylic acid, and cyclopentyl carboxylic acid.

The collector compositions of the invention may be used to remove impurities from a non-sulfide mineral ores by forming an aqueous slurry of the mineral ore, conditioning the mineral ore slurry with the collector composition of the invention, which is generally prepared by the method described above, and separating the impurities and the collector composition from the mineral ore.

DETAILED DESCRIPTION OF THE INVENTION

The present invention is directed to useful alkyl hydroxamic acids and the production of such useful alkyl hydroxamic acids by the reaction of the methyl or ethyl ester of a fatty acid having 6 to 22 carbon atoms with a hydroxylamine salt and an alkali metal hydroxide in the presence of water, either a hydrocarbon oil or a fatty oil derived from plants, animals or fish, or mixtures thereof, and, preferably, with an optional non-ionic or cationic surfactant. The resulting alkyl hydroxamate salt is subsequently acidified with an acid, and the oil/fat solution of the hydroxamic acid is separated from the aqueous phase, resulting in the formation of a liquid solution or a paste of the hydroxamic acid. The hydroxamic solution or paste can then be used without further modification in the froth flotation of non-sulfide minerals, such as kaolin clays, or can be further diluted with frothers, such as, e.g., pine oil, aliphatic $C_5$ to $C_8$ alcohols, polyglycols, polyglycol ethers, etc., to provide a liquid solution useful in a mineral floatation process.

The hydroxamic acid collector compositions of the invention are produced in high yields, typically greater than 90 percent by weight, and, typically, contain substantially less unconverted starting ester and undesirable side reaction products resulting from transesterification and hydrolysis of the starting ester, such as, for example, carboxylic acids and other carbonyl products, than prior art compositions. As a result, the performance of the collector compositions of the invention is significantly improved when compared to prior art compositions.

The process of the invention for producing alkyl hydroxamic acids eliminates the need for hazardous and expensive recovery steps such as filtration, is relatively rapid, being completed in only 3 to 5 hours, and results in extremely high conversions, i.e., on the order of 90 to 100 percent, due to the elimination of competing transesterification reactions, and, thus, provides higher yields than prior art processes. When the optional surfactant is used in the process of the invention, the amount of the surfactant required is smaller than that required in prior art processes. In contrast to the prior art references discussed above, the use of an oil as a carrier from the beginning of the hydroxamic acid preparation, affords better dispersion of chemicals, better handling of the reactor in large scale manufacture, more uniform heat distribution, higher yields of hydroxamic acid, and better control of the reactions and acidification.

In addition, when utilized in the froth flotation of non-sulfide minerals, the oil solutions of the hydroxamic acids are significantly more effective than prior art compositions, producing higher value mineral recovery yields and grades. In general, the oils used tend to be froth neutral, unlike alcohols, having very little effect on froth. The relative froth neutrality of the oil solutions of the hydroxamic acids allows the use of separate alcohol frothers to independently control the froth phase properties as desired.

With the process of the invention, fatty hydroxamic acids are produced by reacting a methyl or ethyl ester of a fatty acid having 6 to 22 carbon atoms, and, preferably, at least 8 carbon atoms, with a hydroxylamine salt and an alkali metal hydroxide in the presence of water, and an oil, selected from the group of hydrocarbon oils, fatty oils, or mixtures thereof. The reaction proceeds according to the equations:

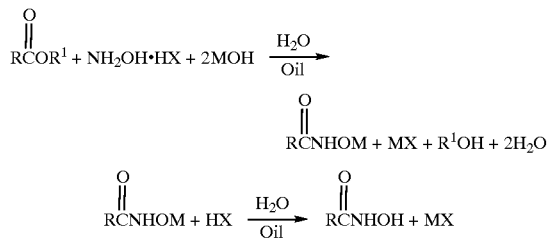

wherein R is a $C_6$ to $C_{22}$ alkyl, a $C_6$ to $C_{10}$ aryl, or a $C_7$ to $C_{14}$ alkaryl group;
M is an alkali metal;
$R^1$ is methyl or ethyl, and
X is a halide, sulfate, bisulfate, phosphate, nitrate or similar anion residue from a mineral acid.

Useful acid esters include the methyl and ethyl esters of such carboxylic acids as caproic acids ($C_6$), enanthic acid ($C_7$), caprylic acid ($C_8$), pelargonic acid ($C_9$), caproic acid ($C_{10}$), undecanoic acid ($C_{11}$), lauric acid ($C_{12}$), tridecanoic acid ($C_{12}$), tridecanoic acid ($C_{13}$), myristic acid ($C_{14}$), pentadeconic acid ($C_{15}$), palmitic acid ($C_{16}$), margaric acid ($C_{17}$), stearic acid ($C_{18}$) and the like, in addition to oleic acid ($C_{18}$), benzoic acid, ethyl benzoic acid, salicylic acid, α- and β-naphthoic acid, cyclohexyl carboxylic acid, cyclopentyl carboxylic acid etc. Ethyl esters of above carboxylic acids may also be used, but require a higher reaction temperature than the methyl esters.

Hydroxylamine salts, such as the sulfate or hydrochloride, can also be used. Suitable alkali metal hydroxides include sodium hydroxide, NaOH, potassium hydroxide, KOH, and the like. Amines such as ammonia, dimethylamine, etc. can be used in place of hydroxides. Suitable acids are hydrochloric, hydrobromic, sulfuric, nitric, etc.

As discussed above, the use of a non-ionic or cationic surfactant is preferred. Examples of useful surfactants include non-ionic surfactants, such as alkyl polyethyleneoxy compounds represented by the formula:

RO(EO)—H, where R is $C_8$ to $C_{18}$ alkyl, EO is ethyleneoxy and n is an integer from 1 to 10, as well as the reaction products of ethylene oxide and higher alkylene oxides with active hydrogen compounds, such as phenols, alcohols, carboxylic acids and amines, e.g., alkylphenoxyethyleneoxy ethanols. Suitable cationic surfactants include alkyl ammonium or quaternary ammonium salts, e.g., tetraalkyl ammonium chloride or bromide, dodecyl ammonium hydrochloride, dodecyl trimethyl quaternary ammonium chloride and the like, and ethoxylated fatty amines. Other suitable surfactants are described in McCutcheon's book of detergents and emulsifiers, the contents of which are incorporated herein by reference. Also included in the aforementioned surfactants are oligomeric and polymerizable surfactants described at pages 319–322 of Blackley, Emulsion Polymerization Theory and Practice, John Wiley and Sons (1975), the contents of which are incorporated herein by reference. Examples of such oligomers include ammonium and alkali metal salts of functionalized oligomers, sold by Uniroyal Chemical under the trade name "Polywet", and copolymers of acrylonitrile and acrylic acid having molecular weights less than 2,000, which are prepared in the presence of chain terminating agents such as n-octyl mercaptan. Examples of polymerizable surfactants include sodium salts of 9- and 10-(acrylamido)stearic acid and the like. The effective amounts of the surfactant range from about 0.5 to 3 percent by weight, of the alkyl ester, preferably about 1 to 2 percent by weight, same basis.

The reaction temperature can range from about 15° to 55° C., preferably from about 25° to 35°. The amount of water used should be sufficient to dissolve the hydroxylamine salt, and can vary from about 15–50 percent, generally depending on the concentration of the hydroxylamine salt solution. The amount of oil used in the reaction can also vary from about 15 to 50 percent, and is preferably sufficient to keep the reaction mixture liquid throughout the course of the reaction at the selected temperature.

The oil can be any suitable oil that will provide the result of the invention, such as hydrocarbon oils, including, but not limited to, an aliphatic hydrocarbons, aromatic hydrocarbons, and mixtures of aliphatic and aromatic hydrocarbons. Preferred hydrocarbon oils include, but are not limited to, benzene, xylene, toluene, mineral oil fractions, kerosene, naphthas, petroleum fractions, and the like. Most preferred hydrocarbon oils are low odor hydrocarbon oils, preferably a paraffin oil, containing less than about 1 percent aromatics. The oil can also be a fatty oil, such as a triglyceride oil, which is an ester of glycerol with fatty acids, substantially free of polar components, such as hydroxyl groups. These triglyceride oils are most often derived from animals, plants or fish by rendering, pressing, or solvent extraction. Fatty oils that can be used include, but are not limited to, soybean oil, corn oil, canola oil, sunflower oil, peanut oil, cod liver oil, shark liver oil, and similar plant, animal and fish oils. The oil used in the present invention can also be a mixture of a hydrocarbon oil and a fatty oil.

When the reaction between the methyl ester and hydroxylamine is complete, and the alkyl hydroxamate salt has been formed, the hydroxamate salt is acidified by the addition of acid, forming two phases, which should be maintained at a temperature sufficiently high to avoid the solidification of the organic product phase. The aqueous phase is then removed decantation or by the method disclosed in U.S. Pat. No. 3,933,872, incorporated herein by reference. The organic phase contains the alkyl hydroxamic acid collector, and is useful as a flotation collector, either as formed or after addition of a frother and/or other additives. Useful frothers include pine oil, aliphatic $C_5$ to $C_8$ alcohols, polyglycols, polyglycol ethers, etc. Other types of additives may be also incorporated into the diluent system specifically to improve performance. Examples of useful additives include petroleum sulfonates, sulfosuccinates, ethoxylated or propoxylated alcohol surfactants, etc., which boost the performance of alkyl hydroxamic acids.

The present invention is also directed to the novel compositions produced by the above-described process. The compositions of the invention comprise a fatty hydroxamic acid, a hydrocarbon oil or fatty oil, and, optionally, a frother or other additive incorporated into the diluent system to improve performance. Where a surfactant is used in the production of the fatty hydroxamic acids of the invention, residual surfactant may also be present in the composition. The alkyl hydroxamic acid content ranges from about 5 percent to about 70 percent, preferably from about 10 percent to about 50 percent, and the oil content ranges from about 10 percent to about 95 percent, preferably from about 20 percent to about 70 percent. If frothers are added, they may be used in an amount of up to about 70 percent of the total composition, preferably in the range of about 10 to about 50 percent. If other additives are incorporated to boost the performance, they may be used in amounts ranging up to about 20 percent of the diluent, preferably about 5 about 10 percent.

The above-described compositions are useful in the froth flotation of non-sulfide mineral ores, such as those mentioned above, including copper ores, iron ores, rare and rare earth metal ores, and, more particularly, in the benefication of clays.

Useful flotation methods are well established, and are known to those of ordinary skill in the art. The methods generally comprise grinding of ore to liberate mineral values and provide ore particles having a size suitable for flotation. The ground ore pulp is pH adjusted, and conditioned with pre-selected and prescribed reagents, such as collectors, frothers, modifier, and dispersants. With some ores, such as glass sands, clays, tailing, etc., the as-mined feed material is already finely divided and, therefore, no additional grinding is required.

In the case of the beneficiation of clays, for example, substantially no grinding of the as-mined feed is required, because the average particle size is of the order of a few microns. The major impurities in kaolin clays are anatase, $TiO_2$, and complex iron minerals, which impart color to the clay, and decrease its brightness, thus making the clay unsuitable for many of its applications where purity and brightness are absolutely essential. Conventionally, the removal of such impurities is accomplished by a variety of methods, an important one being flotation using tall oil fatty acid.

In the froth flotation for beneficating clay, where the clay is slurried in an aqueous medium, conditioned with an effective amount of a dispersing agent and collector, and floated, the method of the invention comprises employing as the collector the novel compositions above, i.e., the hydroxamic acid solution, in quantities ranging from about 0.1 to about 18 pounds per ton of ore, preferably 0.5 to 6 pounds per ton. The novel process of the present invention results in the recovery of clays in high yields, having low $TiO_2$ content and increased brightness.

As a first step in carrying out such a process, the clay to be purified is blunged in water, i.e., mixed with water to form a suspension, at an appropriate solids concentration, as described in U.S. Pat. No. 4,629,556, the contents of which are incorporated herein by reference. A relatively high pulp density, in the range of about 35 to about 70 percent by weight solids, is preferred since the interparticle scrubbing action in such pulp helps liberate colored impurities from the surfaces of the clay particles.

Following conventional practice, a suitable dispersant, such as sodium silicate, polyacrylate, or polyphosphate, is added during blunging in an amount, e.g., about 1 to about 20 lb. per ton of dry solids, sufficient to produce a well-dispersed clay slip. An alkali, such as ammonium hydroxide, is also added, as needed, to produce a pH above about 6, and preferably is the range of about 8 to about 10.5. In accordance with the invention, the hydroxamate collector is then added to the dispersed clay under conditions, i.e., proper agitation speed, optimum pulp density, and adequate temperature, which permit reaction between the collector and the colored impurities of the clay in a relatively short time, generally not longer than about 5 to about 15 minutes.

When the clay has been conditioned after the addition of collector, it is transferred to a flotation cell, and typically diluted to a pulp density that is preferably in the range of about 15 to about 45 percent by weight solids. The operation of the froth flotation machine is conducted in conventional fashion. After an appropriate period of operation, during which the titaniferous impurities are removed with the foam, the clay suspension remaining in the flotation cell can be leached for the removal of residual iron oxides, filtered, and dried in any conventional fashion known in the art.

EXAMPLES

The following non-limiting examples are merely illustrative of the preferred embodiments of the present invention, and are not to be construed as limiting the invention, the scope of which is defined by the appended claims. All parts and percentages are by weight unless otherwise specified.

Comparative Example A

Following the procedure of Wang, as set forth in U.S. Pat. No. 4,871,466, for comparative purposes, 107 parts of hydroxylamine sulfate were dissolved in 264.4 parts of water in a suitable three-neck reaction vessel equipped with a condenser, a mechanically-driven stirrer and a thermometer. After the hydroxylamine sulfate was dissolved, 273.8 parts of dodecyl alcohol, 4.8 parts of a 50 percent dioctyl/decyl dimethyl ammonium chloride surfactant, and 200 parts of methyl caprylate/caprate, the starting ester, were introduced. The reaction mixture was cooled to 10–15° C. with stirring in an ice/water bath, and 200 parts of a 50 percent sodium hydroxide (NaOH) solution was added slowly through an addition funnel. During the addition of sodium hydroxide, the temperature was maintained at 15 to 20° C. After the caustic addition, the temperature was allowed to rise to 25° C., and the reaction was continued for 4 to 5 hours at 25 to 30° C. At the completion of the reaction, i.e., when the IR spectrum of the reaction mixture showed no trace of the ester band at 1175 $cm^{-1}$, 225.4 parts of 30 percent sulfuric acid were added to the reaction mixture, and two phases formed and were separated. A titration analysis of the upper organic layer (513.7 parts), a solution of the hydroxamic acid in dodecyl alcohol, indicated 32 percent hydroxamic acid in contrast to the theoretical yield of 39.2 percent, representing an 81.7% yield based on the amount of starting ester. An NMR analysis indicated the presence of other components in the organic layer, including 7.1 percent by weight of the unreacted methyl caprylate/caprate, 8.6 percent by weight $C_8$ to $C_{10}$ carboxylic acids derived from the starting methyl esters, and 7.1 percent by weight of other carbonyl components derived from the starting ester, where the percentages are based only on the total weight of hydroxamic acid, unreacted ester, and other reaction products in the alcohol solvent. The hydroxamic acid amount was 77.2 percent.

Comparative Example B

Following the procedure described in Russian patent 513,970 for comparative purposes, 992 parts of an aqueous 12 percent solution of hydroxylamine sulfate were introduced into a suitable three-neck reaction vessel equipped with a condenser, a mechanically-driven stirrer, and a thermometer. Following the addition of the hydroxylamine sulfate solution, 168.5 parts of methyl caprylate/caprate were added, followed by the slow addition with stirring of 162.4 parts of a 50 percent sodium hydroxide solution through an addition funnel over a period of 30 minutes. During the addition of the sodium hydroxide, the temperature was maintained at 26° to 28° C. After the caustic addition, the reaction was continued for 2 hours, while continuing to maintain the temperature at 26° to 28° C. After the two hour hold period, 79.46 parts of concentrated sulfuric acid (96.4%) were added slowly, and the temperature was allowed to increase to 40° C. to keep the resulting hydroxamic acid in liquid form. At this time, 169.5 parts of kerosene were added, and the acid/kerosene layer was separated from the bottom aqueous layer. The product layer (344.85 parts) was analyzed by titration, and found to contain 17.4 percent by weight hydroxamate in contrast to the theoretical yield of 50 percent by weight, representing a 35% yield of alkyl hydroxamic acid. The percentage of hydroxamic acid was 35%, of other carbonyl components was 14% and of starting ester was 51%, as determined by NMR. The weight ratio of starting ester to alkyl hydroxamic acid, as measured using NMR analysis, was 1.46 to 1.

Comparative Example C

The process of Comparative Example B was repeated using 496 parts of a 12 percent hydroxylamine sulfate solution, 84.25 parts methyl caprylate/caprate, 81.2 parts of a 50 percent NaOH solution, and 39.73 parts sulfuric acid. Again the temperature after the addition of sulfuric acid was allowed to rise to 40° C., and 211.9 parts of kerosene were added. The upper organic layer was separated from the aqueous layer and analyzed by titration, indicating a 10.54 percent by weight yield of hydroxamate in contrast to the theoretical yield of 28.57 percent by weight, representing a 37 percent yield. The NMR analysis showed 37% hydroxamic acid, 13% other carbonyl components and 50% starting ester. The weight ratio of starting ester to alkyl hydroxamic acid, as measured using NMR analysis, was 1.36 to 1.

Example 1

In a suitable three-neck reaction vessel, equipped with a condenser, a mechanically-driven stirrer, and a thermometer, 1627 parts of hydroxylamine sulfate were dissolved in 4066 parts of water, and 4145 parts of soybean oil, 67 parts of a 50 percent dioctyl/decyl dimethyl ammonium chloride surfactant, and 3036 parts of methyl caprylate/caprate were introduced. The reaction mixture was cooled to about 10 to about 15° C. with stirring in an ice/water bath, and 3028 parts of 50 percent sodium hydroxide was then added slowly through an additional funnel maintaining the temperature at about 15 to about 20° C. throughout the addition. After the addition of the sodium hydroxide, the temperature was allowed to rise to 25° C., and the reaction was continued for about 4 to 5 hours at a temperature of about 25 to about 30° C. The completion of the reaction was determined from the IR spectrum of the reaction mixture, which showed no trace of the ester band at 1175 cm$^{-1}$. Two phases were formed by the addition of 5120 parts of 18.76 percent sulfuric acid, and separated, while maintaining the temperature above the solidification temperature of the hydroxamic acid, e.g., about 30° to 40° C. The upper organic layer, 7719 parts, was found to contain 38.5 percent by weight free hydroxamic acid, corresponding to a 97.5 percent yield, when compared to the theoretical yield of 39.5 percent. Only traces of starting methyl ester and acids derived by hydrolysis were present, as evidenced by the high yield of product. The organic solution, which was obtained by phase separation, was compatible with tall oil fatty acids, contained capryl/capra hydroxamic acid in soybean oil, and was liquid at temperatures above about 30° C., and a paste at lower temperature.

Example 2

The procedure described in Example 1 was repeated. However, following the acidification and separation of the phases, 1281 parts of alcohol frother MIBC were added. The resulting liquid product had a hydroxamic acid of content of 32.7 percent, and remained liquid at a temperature of 20° C. The liquid product was again found to be compatible with tall oil fatty acid.

Example 3

The procedure of Example 1 was repeated, replacing the soybean oil being with hydrocarbon oil, Escaid 110. Following phase separation, the hydroxamate content of the resulting oil solution was 39 percent, representing a 98.7 percent yield of hydroxamic acid. NMR analysis showed the presence of less than 3 percent starting ester and carboxylic acid. The product was substantially free of starting ester, having a weight ratio of unconverted starting ester to alkyl hydroxamate of only 0.02 to 1. The solidification point of the product was 32° C.

Example 4

The procedure of Example 1 was repeated, replacing the soybean oil with a corn oil. Following phase separation, the hydroxamate content of the resulting oil solution was 38.9 percent, representing a 98.5 percent yield of hydroxamic acid, and the solidification point was about 30° C.

Examples 5–8

The procedure of Example 1 was again followed, except that the methyl caprylate/caprate was replaced by an equivalent amount of methyl stearate, Example 5, ethyl oleate, Example 6, methyl palmitate, Example 7, or methyl napththolate, Example 8. Similar conversions of the methyl esters to hydroxamic acids were achieved, and solidification point were similar to those obtained in Example 1.

Examples 9–15

Four thousand parts of fresh kaolin dry basis were blunged at about 60 percent solids for six minutes in a laboratory Morehouse Cowles Dissolver, Model: W12, with water and 6 parts of sodium silicate. A prescribed amount of collector, along with AEROFROTH™ 70 Frother, was then added to the well dispersed clay slurry, and the mixture was conditioned in the same blunger for an additional six minutes.

After conditioning, the entire pulp was diluted with water to 20 percent solids. A sufficient amount of the diluted pulp was taken to provide 2000 parts of fresh kaolin clay in a 4.5 liter laboratory Denver flotation cell. Flotation was carried out at 20 percent solids by carefully regulating the air flow for up to 15 minutes while agitating at 1200 rpm.

Flotation of this kaolin clay sample, designated Sample A, was significantly improved with the novel collectors of the present invention, Examples 9 to 14, when compared to the plant standard co-collector system, which is a 1/1 combination of tall oil with a collector made in accordance with U.S. Pat. No. 4,871,466, a commercial alkyl hydroamate collector product used in Example 15. The results of the comparison are provided in Table I.

TABLE I

Results of Denver Flotation Test Work on Kaolin Sample A

| EXAMPLE | COLLECTOR | | FROTHER | | YIELD | $TiO_2$ |
|---|---|---|---|---|---|---|
| No. | Type | Lbs/T | Type | Lbs/T | % | % |
| 9 | 1:1 Ex. 3/Fatty Acid | 2 | AF-70 | 0.25 | 80.1 | 0.801 |
| 10 | 1:1 Ex. 3/Fatty Acid | 4 | AF-70 | 0.25 | 82.4 | 0.538 |
| 11 | Example 3 | 2 | AF-70 | 0.25 | 84.7 | 0.440 |
| 12 | Example 3 | 1 | AF-70 | 0.50 | 95.6 | 0.548 |
| 13 | 1:1 Ex. 1/Ex. 3 | 1.5 | AF-70 | 0.50 | 74.3 | 0.501 |
| 14 | Example 1 | 1.25 | AF-70 | 0.25 | 87.6 | 0.346 |
| 15 | commercial collector | 1 | Tall Oil | 1 | 83.6 | 0.800 |

TABLE II

Characteristics of Clay Samples B, C and D

| Crude Type | Crude ID No. | GE Bright | $TiO_2$ | Fe % | % Passing 2.0 nm | % Pass 0.2 nm |
|---|---|---|---|---|---|---|
| Fine | C | 82.81 | 2,446 | 1.375 | 87.7 | 46.4 |
| Coarse | B | 84.38 | 1.730 | 0.357 | 63.8 | 15.2 |
| Coarse | D | 84.74 | 1.783 | 0.781 | 76.5 | 23.5 |

A Premier Mill Agitator blunger was used to blunge 796 parts of fresh wet kaolin clay, equivalent to about 651 parts dry solids, with water and 1.3 parts of sodium silicate at 60 percent solids for 6 minutes. A prescribed amount of collector, either a collector of the present invention or a prior art collector for comparison purposes, was then added to the well dispersed clay slurry, and the mixture was conditioned in the blunger for an additional 6 minutes. The conditioned pulp was then transferred to a 2.3 liter flotation cell, diluted with water to about 25 percent solids, agitated at 1000 rpm, and floated with a carefully regulated air flow in the range of about 0.1 to 1.5 l/min of air for up to about 30 minutes.

The floated product containing colored impurities, mostly titaniferous minerals and anatase impurities, and the unfloated cell product, containing the clean and bright clay values, were filtered, dried, and assayed for $TiO_2$ and $Fe_2O_3$. The results are set forth in the Table III below:

TABLE III

| Example No. | Collector | Clay Sample | Solids % | Na. Sil. Lb/T | NaOH Lb/T | Pulp pH | Temp ° C. | Coil Lb/T | Na. Sil. Lb/T | NaOH Lb/T | Pulp pH | Temp ° C. | GE Bright | Yield % | $TiO_2$ % | $Fe_2O_3$ % |
|---|---|---|---|---|---|---|---|---|---|---|---|---|---|---|---|---|
| | None | B | | | | | | | | | | | 84.4 | 100.0 | 1.730 | 0.357 |
| 17 | Example 2 | B | 60.0 | 2.6 | 3.1 | 8.2 | 54.0 | 2.5 | 0.0 | 2.3 | 8.9 | 62.0 | 88.5 | 59.8 | 0.389 | 0.398 |
| 18 | 85:15 Ex. 3/ MIBC | B | 60.0 | 1.8 | 3.1 | 8.1 | 52.0 | 2.5 | 0.0 | 2.3 | 9.0 | 64.0 | 89.6 | 53.3 | 0.238 | 0.379 |
| 19 | Example 3 | B | 60.0 | 1.8 | 3.1 | 8.3 | 52.0 | 2.5 | 0.0 | 2.3 | 9.1 | 58.0 | 89.8 | 46.7 | 0.261 | 0.367 |
| 20 | Tall Oil | B | 60.0 | 1.8 | 3.1 | 8.2 | 54.0 | 2.5 | 0.0 | 2.3 | 9.0 | 56.0 | 88.7 | 38.3 | 0.476 | 0.387 |
| 21 | commercial | B | 60.0 | 1.8 | 3.1 | 8.1 | 52.0 | 2.5 | 0.0 | 2.3 | 8.9 | 57.0 | 90.4 | 46.7 | 0.245 | 0.397 |
| | None | C | | | | | | | | | | | 82.8 | 100.0 | 2.448 | 1.375 |
| 22 | Example 1 | C | 60.0 | 11.4 | 2.3 | 8.2 | 50.0 | 3.6 | 0.0 | 1.2 | 9.0 | 58.0 | 86.3 | 60.5 | 0.962 | 1.345 |
| 23 | Tall Oil | C | 60.0 | 10.5 | 2.3 | 8.1 | 50.0 | 3.6 | 1.8 | 1.2 | 8.9 | 58.0 | 84.4 | 67.9 | 1.732 | 1.349 |
| 24 | commercial | C | 60.0 | 8.8 | 2.3 | 8.1 | 45.0 | 2.0 | 3.1 | 1.2 | 8.8 | 56.0 | 85.6 | 61.1 | 1.368 | 1.379 |
| 25 | Example 3 | C | 60.0 | 8.8 | 2.3 | 8.2 | 48.0 | 2.0 | 3.1 | 1.2 | 8.9 | 58.0 | 86.8 | 44.7 | 1.168 | 1.351 |
| | None | D | | | | | | | | | | | 84.74 | 100.0 | 1.783 | 0.781 |
| 26 | Example 3 | D | 60.0 | 1.8 | 1.5 | 8.2 | 42.0 | 2.5 | 5.8 | 0.5 | 9.1 | 45.0 | 89.2 | 57.5 | 0.530 | 0.738 |
| 27 | commercial | D | 60.0 | 1.8 | 1.5 | 8.0 | 42.0 | 2.5 | 5.8 | 0.5 | 9.1 | 45.0 | 87.9 | 70.7 | 0.809 | 0.769 |
| 28 | Example 1 | D | 60.0 | 1.8 | 1.5 | 8.2 | 42.0 | 2.5 | 5.3 | 0.5 | 9.2 | 44.0 | 88.2 | 64.2 | 0.657 | 0.744 |
| 29 | Tall Oil | D | 60.0 | 1.8 | 1.5 | 8.2 | 42.0 | 2.5 | 5.3 | 0.4 | 9.2 | 42.0 | 86.2 | 59.9 | 1.060 | 0.783 |

Example 16

The alkyl hydroxamate composition of Example 1 was evaluated at a dosage of 1.25 Lbs./T with 0.25 Lbs./T of AF-70 frother using a laboratory column cell incorporating microcell bubble generator system. The clay yield was 97.8 percent and the $TiO_2$ content of the flotation product was 0.421 percent.

Examples 17–29

Flotation tests were carried out on three additional kaolin clay samples designated here as clay samples B, C and D. These crude clay samples had characteristics as summarized in Table II below:

The results for crude clay sample B demonstrate the superiority of the novel collectors of the present invention over both the standard tall oil fatty acid and the commercial collector of Example 15. The best performer on this crude, based on both product yield and $TiO_2$ reduction, was the composition of Example 2, which produced a clay product with a yield of 60 percent at a $TiO_2$ grade of 0.39 percent, as well as a higher GE brightness.

With fine crude clay sample C, the collectors of the invention again surpassed the flotation performance of both the standard tall oil fatty acid and AP-6493. The best performer with this crude was the collector of Example 1, which produced the greatest reduction in $TiO_2$ level at a comparable product yield of 61 percent.

Coarse crude clay D responded to the standard tall oil floatation very poorly, giving $TiO_2$ reduction of only 0.8 percent, with a product yield of 60 percent. The newly invented collectors, along with the commercial collector, produced much improved flotation performance as compared to the standard fatty acid tall oil system. Both the compositions of Examples 1 and 3 produced significantly better $TiO_2$ reductions than the commercial collector, at 0.53 percent and 0.66 percent, but lower product yields of 58 percent and 64 percent, respectively, as compared to the commercial collector's 0.81 percent $TiO_2$ and 70 percent yield.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

We claim:

1. A collector composition, comprising a mixture of a $C_6$ to $C_{22}$ fatty hydroxamic acid, a low odor paraffin oil with an aromatic content between about 0.00001 and 1 percent, and an amount of starting $C_6$ to $C_{22}$ ester that is less than that of the $C_6$ to $C_{22}$ fatty hydroxamic acid.

2. The collector composition of claim 1, wherein the amount of the starting $C_6$–$C_{22}$ ester present is less than 50 percent of the amount of $C_6$ to $C_{22}$ fatty hydroxamic acid.

3. The collector composition of claim 1, wherein the amount of the starting $C_6$–$C_{22}$ ester present is less than 10 percent of the amount of $C_6$ to $C_{22}$ fatty hydroxamic acid.

4. The collector composition of claim 1, wherein the composition is substantially free of the starting $C_6$–$C_{22}$ ester.

5. The collector composition of claim 1, wherein the hydroxamic acid is present in an amount of from about 5 to about 70 percent by weight, and the oil is present in an amount of from about 10 to about 95 percent by weight, based upon the weight of the composition.

6. The collector composition of claim 5, wherein the hydroxamic acid is present in an amount of from about 10 to about 50 percent by weight, and the oil is present in an amount of from about 20 to about 70 percent by weight, based upon the weight of the composition.

7. The collector composition of claim 1, further comprising between about 0.00001 and about 70 percent by weight of a frother.

8. The collector composition of claim 7, wherein said frother is a $C_5$–$C_8$ alcohol frother.

9. The collector composition of claim 7, wherein the frother is present in an amount of from about 10 to about 50 percent.

10. A method for the removal of impurities from a non-sulfide mineral ores, the method comprising:

forming an aqueous slurry of the mineral ore, conditioning the mineral ore slurry with the mineral collector composition of claim 1, and separating the impurities and the mineral collector composition from the mineral ore slurry.

11. The method according to claim 10, wherein the non-sulfide mineral ore is kaolin clay.

* * * * *